United States Patent
Behnk

(10) Patent No.: US 9,623,416 B2
(45) Date of Patent: Apr. 18, 2017

(54) CUVETTE MODULE HAVING AN ELECTRICALLY CONDUCTIVE CUVETTE CARRIER

(76) Inventor: Holger Behnk, Hamburg (DE)

( * ) Notice: Subject to any disclaimer, the term of this patent is extended or adjusted under 35 U.S.C. 154(b) by 473 days.

(21) Appl. No.: 14/122,848

(22) PCT Filed: Jun. 22, 2012

(86) PCT No.: PCT/EP2012/062159
§ 371 (c)(1),
(2), (4) Date: Nov. 27, 2013

(87) PCT Pub. No.: WO2013/004523
PCT Pub. Date: Jan. 10, 2013

(65) Prior Publication Data
US 2014/0090465 A1    Apr. 3, 2014

(30) Foreign Application Priority Data
Jul. 7, 2011 (EP) .................... 11173047

(51) Int. Cl.
*B01L 9/06* (2006.01)
*B01L 3/00* (2006.01)
*G01F 23/24* (2006.01)
*G01N 33/49* (2006.01)

(52) U.S. Cl.
CPC ........... *B01L 9/06* (2013.01); *B01L 3/508* (2013.01); *G01F 23/24* (2013.01); *G01N 33/4905* (2013.01)

(58) Field of Classification Search
CPC ................ B01L 9/06; B01L 2200/16
USPC ...... 73/863.31–863.33, 864.91; 422/72, 400, 422/82.05, 82.09, 102
See application file for complete search history.

(56) References Cited

U.S. PATENT DOCUMENTS

| 5,238,854 A * | 8/1993 | Behnk | G01N 33/4905 435/13 |
| 5,315,872 A | 5/1994 | Moser | |
| 5,622,872 A * | 4/1997 | Ribi | G01N 33/542 204/403.01 |
| 5,993,741 A * | 11/1999 | Behnk | G01N 35/04 422/63 |

(Continued)

FOREIGN PATENT DOCUMENTS

| DE | 102008043412 | 5/2010 |
| EP | 0369168 | 12/1989 |

(Continued)

OTHER PUBLICATIONS

Search Report.

*Primary Examiner* — Michael A Lyons
*Assistant Examiner* — Hoang Nguyen
(74) *Attorney, Agent, or Firm* — Alix, Yale & Ristas, LLP

(57) ABSTRACT

A cuvette module comprises a cuvette carrier and a cuvette held by the cuvette carrier. An intermediate chamber is formed in the cuvette carrier. The cuvette carrier comprises an electrically conductive plastic material. The cuvette has a different material than the cuvette carrier and the wettability of the cuvette carrier is greater than the wettability of the cuvette. A method transfers a predetermined amount of liquid from a transport container to a cuvette, employs a cuvette module. The method makes it easier to check whether the intermediate chamber still contains a sufficient amount of liquid.

12 Claims, 3 Drawing Sheets

(56) References Cited

U.S. PATENT DOCUMENTS

| | | | |
|---|---|---|---|
| 6,746,582 B2 * | 6/2004 | Heller | G01N 27/3271 204/403.05 |
| 7,858,387 B2 * | 12/2010 | DiCesare | B01L 3/5085 250/281 |
| 2001/0055669 A1 * | 12/2001 | Schultz | B01J 19/0046 428/173 |
| 2002/0172789 A1 * | 11/2002 | Watson | B82Y 10/00 428/36.91 |
| 2002/0182110 A1 * | 12/2002 | Behnk | B01L 3/502 422/72 |
| 2006/0165565 A1 * | 7/2006 | Ermakov | B01J 19/0046 422/130 |
| 2007/0154922 A1 * | 7/2007 | Collier | B01L 3/50273 435/6.1 |
| 2009/0004064 A1 | 1/2009 | Liu et al. | |
| 2009/0232707 A1 * | 9/2009 | Behnk | B01F 13/0818 422/400 |

FOREIGN PATENT DOCUMENTS

| | | |
|---|---|---|
| EP | 1116953 | 7/2001 |
| EP | 1867986 | 12/2007 |
| EP | 1992952 | 11/2008 |

\* cited by examiner

CUVETTE MODULE HAVING AN ELECTRICALLY CONDUCTIVE CUVETTE CARRIER

BACKGROUND

The invention relates to a cuvette module, comprising a cuvette carrier and a cuvette held by the cuvette carrier. An intermediate chamber is formed in the cuvette carrier. The invention further relates to a method for transferring a predefined amount of liquid from a transport container to a cuvette.

Cuvette modules of this kind can be used in the analysis of liquids, particularly in the analysis of body fluids. For the analysis, it is necessary to transfer a precisely metered amount of the liquid from a transport container to the cuvette. Since the transport containers may be subject to an overpressure or underpressure, it is not altogether easy to remove a defined amount of liquid directly from the transport container. This applies in particular when dealing with small amounts of liquid. It is thus known to introduce the liquid firstly into an intermediate chamber and to measure off the amount of liquid precisely from the intermediate chamber (see EP 1 867 986).

That the predefined amount of liquid can be removed from the intermediate chamber presupposes that the amount of liquid that was previously transferred from the transport container to the intermediate chamber is greater than the predefined amount of liquid. Therefore, before the removal of the predefined amount of liquid from the intermediate chamber, the filling level in the intermediate chamber is measured. Only if enough liquid is contained in the intermediate chamber can the predefined amount of liquid be removed. If there is too little liquid in the intermediate chamber, this is an indication of an error.

One possible way of measuring the filling level in the intermediate container is to bring an electrical sensor to the surface of the liquid and to conclude from a change of the electrical signal that the sensor is immersed in the liquid. When the intermediate chamber is made of a plastics material, as is generally the case, distorted measurement results often arise.

SUMMARY

An object is to make available a cuvette module and an associated method that both facilitate the metering of small amounts of liquid. Briefly stated, the cuvette carrier is made of an electrically conductive plastics material. The cuvette is made of a different material than the cuvette carrier, and the wettability of the cuvette carrier is greater than the wettability of the cuvette.

A number of terms are first explained. Within the context of the invention, a cuvette designates a container into which a metered amount of liquid can be introduced in order to perform analyses on the liquid. The liquid can be a body fluid. One possible application is the measurement of the blood clotting time (see EP 0 369 168).

Intermediate chamber designates a structure of the cuvette carrier in which a liquid can be received when the chamber is in a suitable orientation. The intermediate chamber is not generally closed on all sides, and therefore the liquid flows out of the intermediate chamber when the cuvette module is turned upside down. The intermediate chamber is a component part of the cuvette carrier, which means that the walls of the intermediate chamber are made of electrically conductive plastic. The word "intermediate" expresses the fact that the intermediate chamber can be used to receive a liquid on a temporary basis. No structural limitation is intended by this.

An advantage is that the electrical conductivity of the plastics material means that interference signals are avoided. It is therefore possible, by immersion of an electrical sensor, to determine the filling level of the liquid in the intermediate chamber. It can thus be easily ensured that enough liquid is contained in the intermediate chamber before the predefined amount of liquid is removed and transferred to the cuvette.

Plastics are generally insulators with no or only very slight electrical conductivity. To proceed from such a plastic and arrive at an electrically conductive plastics material of the kind suitable, the plastics material can be filled with electrically conductive particles. To achieve a high degree of conductivity, the particles are added to the plastics material preferably in a concentration which ensures that the particles are only at a short distance from one another or even touch one another. The electrically conductive plastics material is preferably adapted such that the resistivity of the material at room temperature is less than 106 Ωcm.

If electrical interference signals are to be avoided, the surface resistance in particular should be low. The surface resistance designates the resistance that is measured between two electrodes applied to the surface of the material. The surface resistance depends on the geometry of the cuvette carrier and on the positioning of the electrodes on the cuvette carrier. The values for the surface resistance relate to a measurement carried out as follows. A respective metal electrode is inserted into each of two adjacent intermediate chambers, said electrode being in planar contact with three walls of the intermediate chamber. The three walls can be two side walls and the bottom. The electrical resistance between the two electrodes is measured. The surface resistance according to this measurement is preferably between 1 kΩ and 50 kΩ, more preferably between 5 kΩ and 30 kΩ, more preferably between 9 kΩ and 14 kΩ.

From the filling level in the intermediate chamber, the amount of liquid can be reliably deduced only if the intermediate chamber is completely wetted by the liquid. Generally, in plastics materials of the kind used as the starting material for the electrically conductive plastic, the wettability of the surface is not particularly great. Consequently, water forms pronounced droplets on the surface, instead of spreading across the latter. With poor wettability of the surface of the electrically conductive material, there is the risk of air inclusions forming in the intermediate chamber, with the result that the amount of liquid can no longer be deduced from the filling level. It has been found that the wettability of the plastics material can be improved if a suitable conductive filler material is used. Possible filler materials are in particular graphite or conductive carbon black particles. When these particles reach as far as the surface of the plastics material, i.e. when part of the surface is formed by these particles, this results in considerably improved wettability.

By contrast, as regards the cuvette into which the liquid is transferred from the intermediate chamber, a high degree of wettability is not in fact desirable. The reason is that, during the analysis, the liquid is in most cases mixed together with a second liquid. To prevent the liquids from already mixing before the analysis, it is advantageous if the liquid forms very pronounced droplets on the surface. For this reason, the cuvette is made of a different material than the cuvette carrier, wherein the wettability of the cuvette carrier is greater than the wettability of the cuvette. The wettability can be measured by measuring the angle that a droplet encloses with the surface. The wetting angle of the cuvette is preferably greater than the wetting angle of the cuvette carrier by at least 10°, more preferably by at least 30°, more preferably by at least 45°.

The cuvette module is generally used in the analysis of small amounts of liquid. The size of the cuvette module should be adapted to the amounts of liquid. Thus, the intermediate chamber preferably has a volume of between 10 µl and 500 µl, more preferably a volume of between 50 µl and 250 µl. The cuvette module can be designed such that several analyses can be performed in one run. For this purpose, the cuvette module can comprise a plurality of cuvettes. The number of intermediate chambers is preferably equal to the number of cuvettes. To facilitate the automatic handling of the cuvette module, it is possible to provide the cuvette module with an arrangement of teeth in which a toothed wheel of a machine can engage.

A predefined amount of liquid from a transport container to a cuvette is disclosed. In the method, an amount of liquid greater than the predefined amount of liquid is first of all transferred from the transport container to an intermediate chamber, wherein the intermediate chamber is made of an electrically conductive plastics material. The filling level in the intermediate chamber is determined by inserting an electrical sensor into the intermediate chamber and establishing a change of the electrical signal when the electrical sensor dips into the liquid. A check is made to establish whether the amount of liquid in the intermediate chamber is greater than the predefined amount of liquid, and an error message is output if this is not the case. The predefined amount of liquid is then removed from the intermediate chamber and transferred to the cuvette.

The predefined amount of liquid can be removed from the intermediate chamber by means of a hollow needle. The hollow needle can serve at the same time as an electrical sensor. The hollow needle can be a component part of a resonant circuit operated at resonant frequency. The oscillation behavior changes when the hollow needle is immersed in the liquid. The method can be developed with further features that have been described above with reference to the cuvette module.

BRIEF DESCRIPTION OF THE DRAWINGS

The invention is described by way of example below on the basis of advantageous embodiments and with reference to the attached drawings, in which.

DETAILED DESCRIPTION

Figure 1:
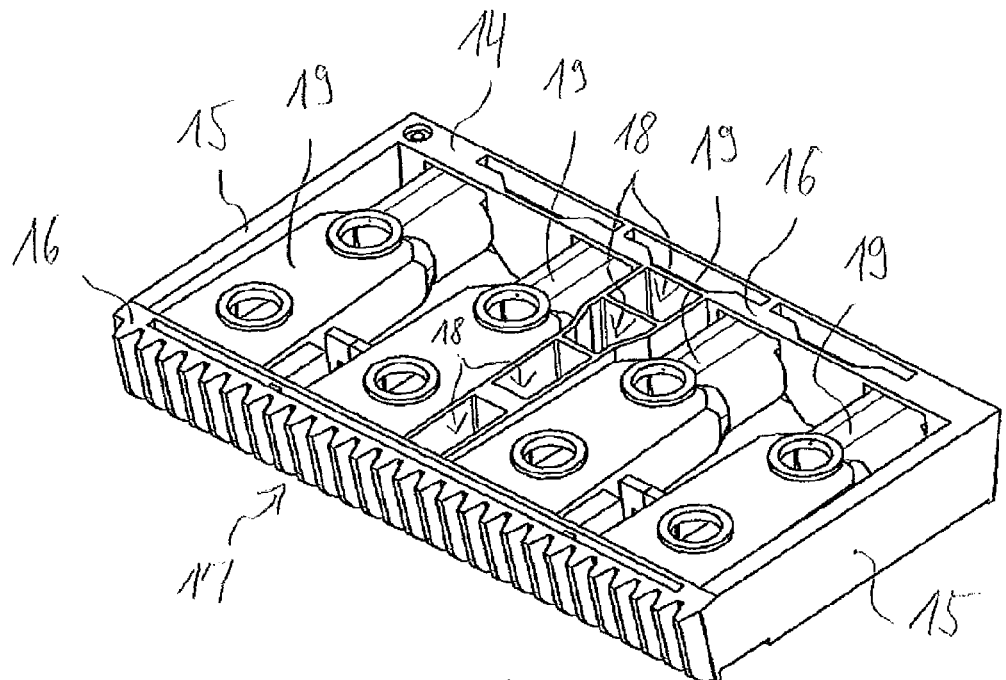
FIG. 1 shows a perspective view of a cuvette module.
Figure 2:
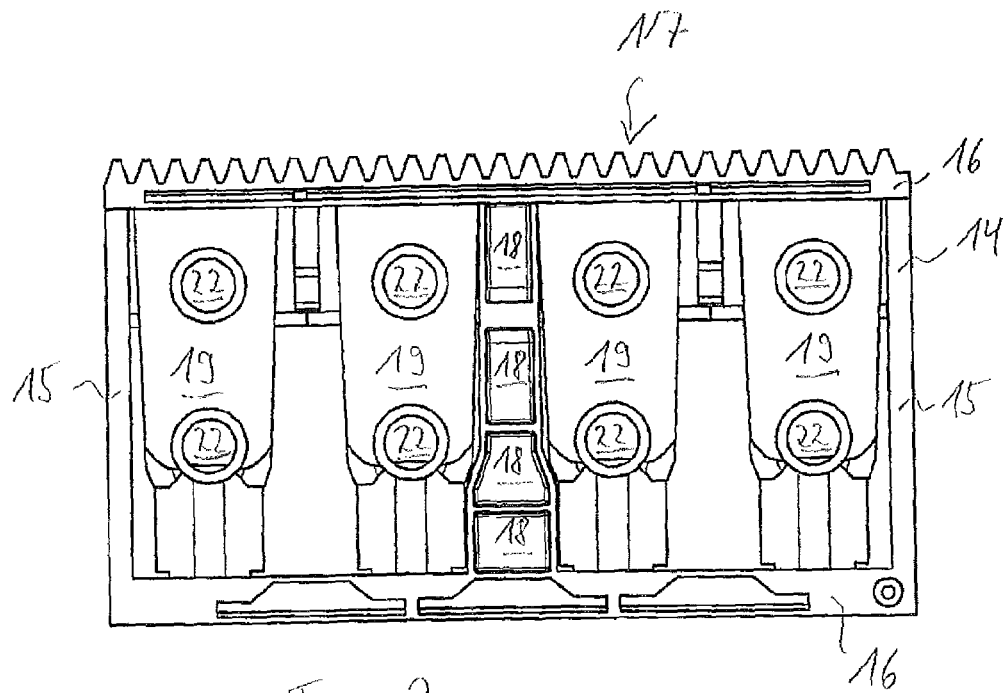
FIG. 2 shows the cuvette module from FIG. 1 in a view from above.

In FIG. 1, a cuvette module comprises a cuvette carrier 14, which forms an outer frame composed of two transverse webs 15 and two longitudinal webs 16. One of the longitudinal webs 16 is provided with an arrangement of teeth 17, by means of which the cuvette module can be precisely positioned when it is guided on a rail.

In the center between the two transverse webs 15, the cuvette carrier 14 comprises an arrangement of four intermediate chambers 18. The cuvette carrier 14 with the two transverse webs 15, the two longitudinal webs 16 and the intermediate chambers 18 is formed in one piece and is made of an electrically conductive plastics material. The conductivity is achieved by filling a non-conductive plastics starting material with a sufficient content of conductive carbon black particles.

The cuvette carrier 14 is also equipped with seats for four cuvettes 19. The four cuvettes 19 are produced as injection molded parts and are made of a plastics material customary for this purpose. The four cuvettes 19 are connected to one another by a connector web (not visible in FIG. 1) and are locked as a unit into the seat of the cuvette carrier 14. Both the cuvette 19 and also the cuvette carrier 14 are preferably made of a material that does not react with body fluids such as blood.

Figure 3:
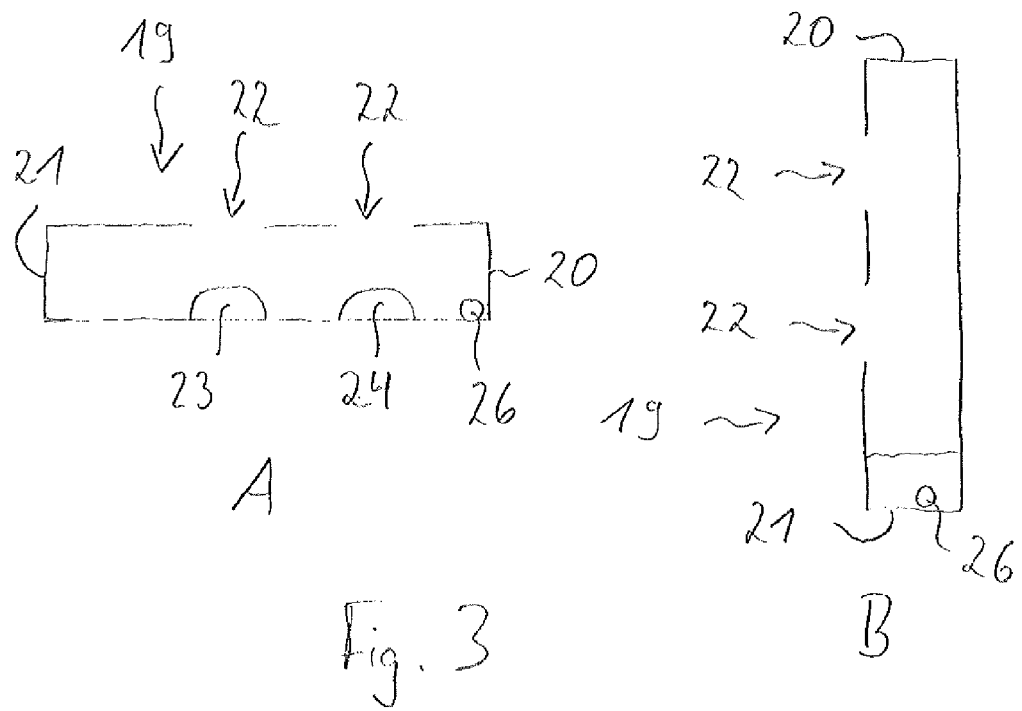
FIG. 3 shows a schematic cross-sectional view of a cuvette in two different positions.
Figure 4:
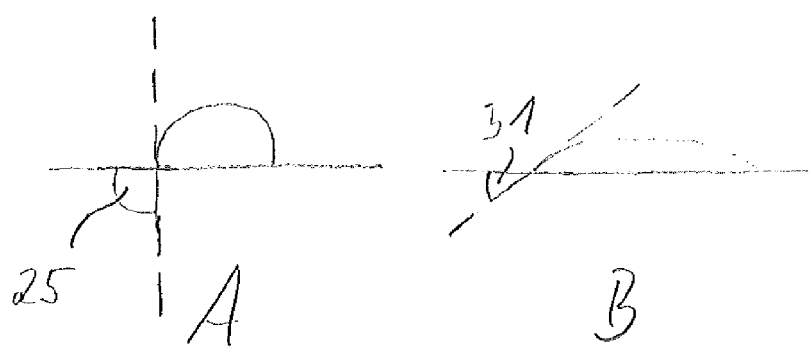
FIG. 4 shows two different wetting angles.

According to FIG. 3, the cuvettes 19 each extend from an upper end 20, which faces in the direction of the teeth 17 in FIG. 1, to a lower end 21, which adjoins the opposite longitudinal web 16. Each cuvette 19 has two openings 22 through which small amounts of liquid 23, 24 can be introduced into the cuvette 19 when the cuvette is arranged in a lying position as shown in FIG. 3A. The plastics material of the cuvette 19 has a low wettability, such that the amounts of liquid 23, 24 form pronounced droplets on the surface of the plastics material. The droplets have a large wetting angle 25 which, according to FIG. 4A, is about 90°.

When the cuvette 19 is pivoted through 90° to the position shown in FIG. 3B, the amounts of liquid 23, 24 flow down along the wall and collect at the lower end 21 of the cuvette 19. A ball 26 contained in the cuvette 19 also rolls down and can be used for uniformly mixing the amounts of liquid 23, 24 for the analysis by means of a magnetic stirrer (not shown). The amount of liquid 23 can be blood for example, and the amount of liquid 24 can be a reagent, and the analysis can involve measuring the clotting time.

The blood is normally made available in a closed transport container (not shown) which contains a greater amount of liquid than is needed for the analysis. Since there may be an overpressure or underpressure in the transport container, it is not easy to precisely meter the small amount of liquid 23 needed for the analysis directly from the transport container. For this reason, an amount of liquid greater than the predefined amount of liquid 23 is first of all removed from the transport container and introduced into one of the intermediate chambers 18 of the cuvette carrier 14.

Before the removal of the predefined amount of liquid 23 from the intermediate chamber 18, a check is made to ascertain whether the amount of liquid contained in the intermediate chamber 18 is actually greater than the predefined amount of liquid 23. For this purpose, according to FIG. 5, a hollow needle 27 is inserted from above into the intermediate chamber 18. The hollow needle 27 is connected to an electrical circuit 28 (only represented schematically in FIG. 5) which registers a change of the electrical signal when the hollow needle 27 dips into the liquid. From the filling level, it is established whether a sufficient amount of liquid is contained in the intermediate chamber 18. If this is not the case, an error message is given. If enough liquid is contained in the intermediate chamber 18, the predefined amount of liquid 23 is removed from the intermediate chamber 18 by means of a metering device 29, to which the hollow needle 27 is attached. The hollow needle 27 is then inserted into one of the openings 22 of the cuvette 19, and the predefined amount of liquid 23 is released again.

The intermediate chamber 18 has a capacity of 150 µl, while the amount of liquid 23 to be metered may amount to 20 µl, for example. With such small amounts of liquid, there is a risk of distortion of the electrical signal which is used to establish the immersion of the hollow needle 27 into the liquid. Provision is therefore made that the cuvette carrier 14 and therefore the walls of the intermediate chamber 18 are made of an electrically conductive plastic. It has been found that it is thereby possible to reliably establish the change of the electrical signal upon immersion of the hollow needle 27.

To determine whether an electrically conductive plastics material is suitable as the material for the cuvette carrier 14, a measurement of the surface resistance can be carried out. For this purpose, a respective metal electrode 30 is inserted into each of two adjacent intermediate chambers 18, said electrode 30 being dimensioned such that it bears on two opposite side walls and on the bottom of the intermediate chamber 18. In this measurement, the resistance measured between the two electrodes 30 should be between 9 kΩ and 14 kΩ.

Figure 5:
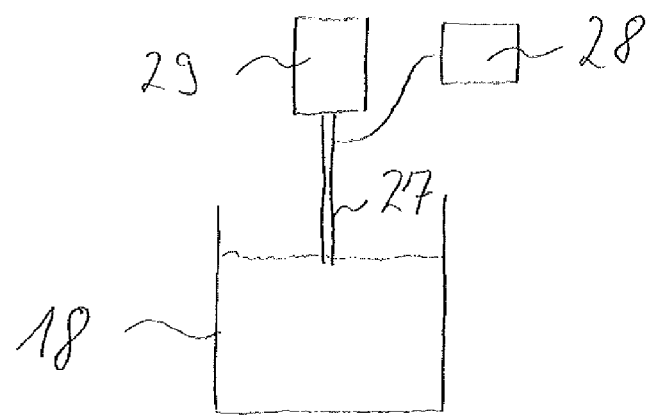
FIG. 5 shows a schematic representation of how a filling level is measured in the intermediate chamber.
Figure 6:
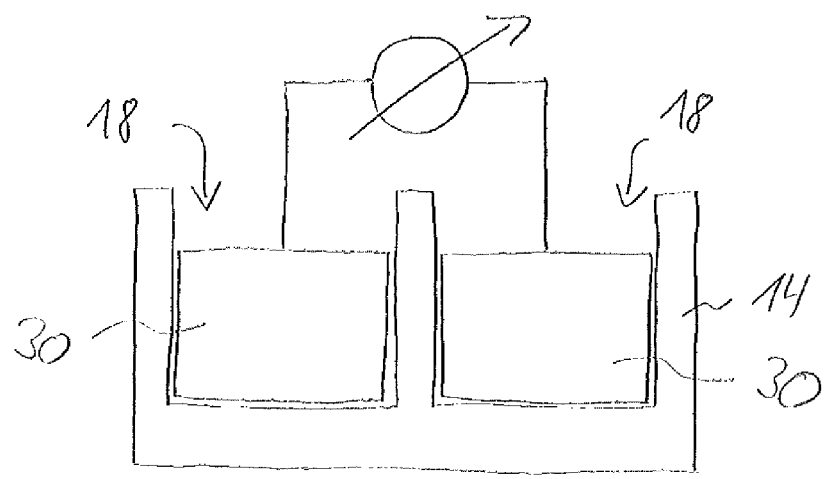
FIG. 6 shows a schematic representation of a method for measuring the surface resistance.

To ensure that the amount of liquid contained in the intermediate chamber 18 can be reliably deduced from the measurement of the filling level shown in FIG. 5, the intermediate chamber 18 has to be filled uniformly with the liquid, and there must be no inclusion of air bubbles. To this end, it is advantageous if the electrically conductive plastics material has a high degree of wettability. An amount of liquid applied to the surface of the material then spreads across a large surface area and does not form a pronounced droplet. The wetting angle 31 shown in FIG. 4B can be 30° for example, and therefore 60° smaller than the wetting angle 25 that the same amount of liquid has on the material of the cuvette 19. The high degree of wettability of the electrically conductive plastics material is a result of the fact that the conductive carbon black particles are distributed in the plastics material such that they form part of the surface of the material.

The invention claimed is:

1. A cuvette module, comprising a cuvette carrier and a cuvette held by the cuvette carrier, with an intermediate chamber formed in the cuvette carrier, characterized in that the cuvette carrier is made of an electrically conductive plastics material, in that the cuvette is made of a different material than the cuvette carrier, and in that the cuvette carrier and the cuvette each have a wettability and the wettability of the cuvette carrier is greater than the wettability of the cuvette and the electrically conductive plastic material has a base material, wherein the base material is a plastic and the wettability of the electronically conductive plastic material is greater than the wettability of the plastic base material.

2. The cuvette module as claimed in claim 1, characterized in that the electrically conductive plastics material has a resistivity and the resistivity of the electrically conductive plastics material at room temperature is less than $10^6$ Ωcm.

3. The cuvette module as claimed in claim 1, characterized in that the cuvette carrier comprises two intermediate chambers lying next to each other, and in that the cuvette carrier has a surface resistance and the surface resistance of the cuvette carrier, measured by two electrodes inserted into the intermediate chambers, is between 1 kΩ and 50 kΩ.

4. The cuvette module as claimed in claim 1, characterized in that the electrically conductive plastics material has a filler and the filler of the electrically conductive plastics material is graphite or conductive carbon black.

5. The cuvette module as claimed in claim 1, characterized in that the cuvette carrier and the cuvette each have a wetting angle and the wetting angle of the cuvette carrier is smaller than the wetting angle of the cuvette by at least 10°.

6. The cuvette module as claimed in claim 1, characterized in that it comprises a plurality of intermediate chambers and a plurality of cuvettes.

7. The cuvette module as claimed in claim 1, characterized in that the intermediate chamber has a volume and the volume of the intermediate chamber is between 1 µl and 500 µl.

8. The cuvette module as claimed in claim 1 characterized in that the cuvette carrier comprises two intermediate chambers lying next to each other, and in that the cuvette carrier has a surface resistance and the surface resistance of the cuvette carrier, measured by two electrodes inserted into the intermediate chambers, is between 5 kΩ and 30 kΩ.

9. The cuvette module as claimed in claim 1 characterized in that the cuvette carrier comprises two intermediate chambers lying next to each other, and in that the cuvette carrier has a surface resistance and the surface resistance of the cuvette carrier, measured by two electrodes inserted into the intermediate chambers, is between 9 kΩ and 14 kΩ.

10. The cuvette module as claimed in claim 1, characterized in that the cuvette carrier and the cuvette each have a wetting angle and the wetting angle of the cuvette carrier is smaller than the wetting angle of the cuvette by at least 30°.

11. The cuvette module as claimed in claim 1, characterized in that the cuvette carrier and the cuvette each have a wetting angle and the wetting angle of the cuvette carrier is smaller than the wetting angle of the cuvette by at least 45°.

12. The cuvette module as claimed in claim 1, characterized in that the intermediate chamber has a volume and the volume of the intermediate chamber is between 50 µl and 250 µl.

* * * * *